US008211136B2

(12) United States Patent
Griffith et al.

(10) Patent No.: US 8,211,136 B2
(45) Date of Patent: Jul. 3, 2012

(54) STOMA DILATOR (75) Inventors: Nathan Christopher Griffith, Roswell, GA (US); Donald Jay McMichael, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 597 days.

(21) Appl. No.: 11/848,502

(22) Filed: Aug. 31, 2007

(65) Prior Publication Data
US 2009/0062832 A1    Mar. 5, 2009

(51) Int. Cl.
    *A61M 29/00* (2006.01)
(52) U.S. Cl. ........................................ 606/191; 606/194
(58) Field of Classification Search .................. 600/184; 606/191, 190, 192, 194, 159; 604/164.01, 604/164.05, 164.1, 164.13, 161, 264
    See application file for complete search history.

(56) References Cited

U.S. PATENT DOCUMENTS

| 4,449,532 | A | | 5/1984 | Storz |
| 4,581,025 | A | | 4/1986 | Timmermans |
| 4,772,266 | A | | 9/1988 | Groshong |
| 4,862,891 | A | | 9/1989 | Smith |
| 4,895,564 | A | * | 1/1990 | Farrell ....................... 604/164.1 |
| 5,074,846 | A | | 12/1991 | Clegg et al. |
| 5,098,392 | A | | 3/1992 | Fleischhacker et al. |
| 5,139,486 | A | | 8/1992 | Moss |
| 5,318,543 | A | | 6/1994 | Ross et al. |
| 5,499,975 | A | * | 3/1996 | Cope et al. ................. 604/164.1 |
| 5,536,255 | A | | 7/1996 | Moss |
| 2003/0208220 | A1 | | 11/2003 | Worley et al. |
| 2004/0098020 | A1 | * | 5/2004 | Nardeo ......................... 606/194 |
| 2005/0080443 | A1 | | 4/2005 | Fallin et al. |
| 2006/0004398 | A1 | * | 1/2006 | Binder et al. ................ 606/191 |
| 2006/0030872 | A1 | | 2/2006 | Culbert et al. |

(Continued)

FOREIGN PATENT DOCUMENTS

EP    0334116 A1    9/1989

(Continued)

OTHER PUBLICATIONS

Patent Cooperation Treaty Search Report from the International Search Authority, International Application No. PCT/IB2008/052422 dated Mar. 11, 2010.

*Primary Examiner* — Ryan Severson
*Assistant Examiner* — Tin Nguyen
(74) *Attorney, Agent, or Firm* — Karl V. Sidor; Sue C. Watson (57) ABSTRACT

A stoma dilator is provided which has a base dilator and a plurality of dilators which are coaxially disposed over the base dilator. The base dilator has a hub and an opening therethrough. The base dilator is configured to be positioned over a wire into a patient's tissue. Each of the plurality of dilators has a tapered distal end, a proximal end, and a tubular body, and are held in separated, telescoping position by the dilator positioner such that a portion of each distal end is exposed from beneath another dilator and is graspable by a health care practitioner for movement such that a smaller diameter dilator does not become inaccessible inside of a larger diameter dilator. The stoma dilator may include a hollow sheath positioned over an outermost dilator. The sheath is configured to hold open a tissue opening created by the plurality of dilators. The base dilator and the plurality of dilators may be removed while the sheath remains in a tissue opening. Another device may be inserted through the sheath, and the sheath may be peeled away therefrom.

9 Claims, 9 Drawing Sheets

U.S. PATENT DOCUMENTS

| | | |
|---|---|---|
| 2006/0052749 A1 | 3/2006 | Moyer |
| 2006/0092694 A1 | 5/2006 | Choi et al. |
| 2006/0203430 A1 | 9/2006 | Pinnow et al. |
| 2006/0217664 A1 | 9/2006 | Hattler et al. |
| 2007/0099405 A1 | 5/2007 | Oliva et al. |

FOREIGN PATENT DOCUMENTS

| | | |
|---|---|---|
| EP | 0383426 A1 | 8/1990 |
| EP | 0475324 A1 | 3/1992 |
| EP | 0935974 B1 | 10/2003 |
| WO | WO 92/08513 | 5/1992 |
| WO | WO 92/20399 | 11/1992 |
| WO | WO 99/17665 | 4/1999 |
| WO | WO 02/087678 | 11/2002 |
| WO | WO 2004/019760 A2 | 3/2004 |
| WO | WO 2006/017507 | 2/2006 |
| WO | WO 2007/000159 | 1/2007 |
| WO | WO 2007/033341 | 3/2007 |

* cited by examiner

STOMA DILATOR

BACKGROUND OF THE INVENTION

This invention relates to devices for enabling sequential percutaneous dilation of a tissue opening to create a stoma to permit subsequent insertion of a large cannula, and enteral feeding tube, and so forth. More particularly, the present invention pertains to a sequential dilator that utilizes a series of telescoping dilators of gradually increasing size.

Although placement of small diameter cannulae is routinely done thousands of times each day in hospitals, medical clinics, and the like, placement of larger cannulae and other larger devices in blood vessels or hollow organs has been limited. More recently, techniques have been developed which enable gradual dilation of a small percutaneous opening to the required large size. Tapered dilators have been developed which are small at the tip and which increase in diameter to a desired dilation radius. Such tapered designs for large cannulae are typically too long for dilatoring hollow organs, such as a patient's stomach. Therefore, introduction of large cannulae by dilators with extreme tapered configuration has not been practical.

Further, techniques developed to overcome this problem have, in turn, created new problems. Some devices that comprises a series of telescoping tubes for stoma dilation have problems. For example, in a multiple tube dilation system, a smaller tube positioned in a larger tube may, at times, frictionally couple to the larger tube, making it difficult or impossible to separate the tubes, particularly after the dilator is positioned in a patient. In other dilator assemblies, telescoping tubes may be slid in both directions in telescoping relationship and pose the problem of smaller tube ends sliding within the bore of a larger tube, thereby making the small tube un-graspable by a health care provider for withdrawal from the assembly. That is, each smaller tube has substantially greater length than the larger tubes, and basically operates as a guide wire for the next tube mounted thereon. This pattern of decreasing the length of the tube with increasing diameter requires a health care provider to guess as to the desired positioning location of each telescoping section. Obviously, there is no guarantee that correct positioning will remain during patient use even if the correct position is initially applied. This unpredictable character not only increases risk to the patient, but also adds difficulty to the attending health care providers.

It would be desirable to have a simple and more reliable approach to patient cannulation which does not depend on the exercise of extreme care by health care providers for proper emplacement of a catheter, an enteral feeding tube, and so forth. Such a device would permit introduction of a series of telescoping tubes of increasing size, each having a short, tapered tip, and each having a radial ring or stop, which would prevent the next larger tube from extending beyond the previous tube. Further, the radial stop would provide sufficient area of the next proceeding tube so that a health care provider could readily grasp the next tube for introduction through the tissue opening.

In such a dilator assembly, an introducer or base dilator would be configured to feed over an initial guide wire placed by an introducer needle. Desirably, at an opposite end of such a base dilator, a spaced-apart series of radially grouped, axially-aligned bars would be positioned to extend from an external circumference of the base dilator. Each group of bars would desirably be of an increasing diameter; preferably, the outer diameter of the next larger tube in the telescoping sequence of tubes. The bars would be separated by a gap. The bars would desirably cooperate with each tube. That is, retaining rings on the tubes would fit into gaps on the bars, while each group of bars would contact an end of a tube which was substantially similar in diameter an outer diameter of the bars. In this manner, the series of telescoping tubes would be encouraged into the proper series of deployment, and this design would decrease the likelihood of two or more tubes frictionally engaging and becoming inseparable either during or after the creation of a patient's stoma.

Such a device also desirably includes a luer lock fitting to permit luminal access to the vessel or organ into which the stoma has been created. A peel-away sheath is desirably provided as part of such a stoma dilator. The peel away sheath, while initially attached to the dilator, would be easily detachable to permit the sheath to retain the desired dilation of the stoma while the dilator was removed. The sheath would then allow another device, such as an enteral feeding tube, to be positioned into the patient via the sheath. The sheath would then be easily detached, desirably split into at least two pieces for removal from the stoma without interference with the remaining device.

DEFINITIONS

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the terms "resilient", "resilience" and/or "resiliency" and any derivatives thereof refers to the physical property of an object and/or a material that can return to its original form, shape and/or position after deformation such as being bent, compressed, or stretched that does not exceed its elastic limit.

As used herein, the term "couple" includes, but is not limited to, joining, connecting, fastening, linking, or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; a significant or great amount; for example, as used herein "substantially" as applied to "substantially" covered means that a thing is at least 70% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated number or a stated or implied range.

As used herein, the phrase "patient's tissue" includes organs, such as, but not by way of limitation, hollow organs such as a patient's stomach or a portion of the intestinal tract, and blood vessels, such as veins and/or arteries.

These terms may be defined with additional language in the remaining portions of the specification.

SUMMARY OF THE INVENTION

In response to the difficulties and problems discussed herein, a stoma dilator is provided. The stoma dilator includes a base dilator having a distal end, a proximal end, and a tubular body positioned therebetween. A hub is positioned on the proximal end of the base dilator, and at least a portion of a dilator positioner is provided therewith. The distal end has a stop thereon, and the base dilator formed to include an opening therethrough. The base dilator is configured to be positioned over a wire into a patient's tissue. The stoma dilator also includes a plurality of dilators coaxially stacked on the base dilator. Each of the plurality of dilators has a tapered distal end, a proximal end, and a tubular body positioned therebetween. Another portion of the dilator positioner is positioned on more than one of the plurality of dilators. The portions of the dilator positioner cooperate to position the plurality of dilators such that a portion of each distal end of each dilator is graspable by a health care practitioner for movement, wherein the stop on base dilator and the stops on the plurality of dilators cooperate to form a continuous taper of a distal end of the stoma dilator when the plurality of dilators are positioned in a deployed position.

In another aspect of the invention, a stoma dilator is provided. The stoma dilator includes a base dilator having a distal end, a proximal end, and a tubular body positioned therebetween. A hub is positioned on the proximal end and at least a portion of a dilator positioner is provided therewith. The base dilator is formed to include an opening therethrough, the base dilator is configured to be positioned over a wire into a patient's tissue. The stoma dilator also includes a plurality of dilators coaxially stacked on the base dilator. Each of the plurality of dilators having a tapered distal end, a proximal end, and a tubular body positioned therebetween. More than one of the dilators is positioned by at least another portion of the dilator positioner such that each distal end is exposed from beneath another dilator and is graspable by a health care practitioner for movement such that a smaller diameter dilator does not become inaccessible inside of a larger diameter dilator.

In another aspect of the invention, a stoma dilator is provided. The stoma dilator includes a base dilator having a distal end, a proximal end, and a tubular body positioned therebetween. A hub is positioned on the proximal end and at least a portion of a dilator positioner is provided therewith. The base dilator is formed to include an opening therethrough. The base dilator is configured to be positioned over a wire into a patient's tissue. The stoma dilator also includes a plurality of dilators coaxially stacked on the base dilator. Each of the plurality of dilators has a tapered distal end, a proximal end, and a tubular body positioned therebetween. More than one of the plurality of dilators includes at least another portion of the dilator positioner such that a portion of each distal end is exposed from beneath another dilator and is graspable by a health care practitioner for movement such that a smaller diameter dilator does not become inaccessible inside of a larger diameter dilator. The stoma dilator further includes a hollow sheath positioned over an outermost dilator of the plurality of dilators. The sheath has a pair of handles at a proximal end which are configured to releaseably couple to the hub. The sheath includes a blunt distal end moveable over an outermost dilator, and a sheath body provided between its proximal end and distal end. The sheath is configured to hold open a tissue opening created by the plurality of dilators such the base dilator and plurality of dilators are removable therefrom. The sheath is configured to permit at least a portion of a device to be inserted therethrough. The sheath is separable via the handles such that slits form through the sheath body to permit the sheath to peel away.

Additional features and advantages of the present invention will be revealed in the following detailed description. Both the foregoing summary and the following detailed description and examples are merely representative of the invention, and are intended to provide an overview for understanding the invention as claimed.

DETAILED DESCRIPTION

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Referring now to FIGS. 1-8, a stoma dilator for enabling the sequential dilation of a tissue opening is illustrated. The stoma dilator 10 includes an introductory or base elongated base or first dilator 12 which includes an first introducer end or first end 14, a proximal end or tail end 16 (FIGS. 6 and 7), and an elongated tubular body 18. The base or first dilator 12 also includes a tapered shoulder 20. The shoulder 20 is formed between the introducer end 14 and intermediate body 18. This shoulder 20 extends or tapers outward from a small diameter of the introducer first end 14 to the larger diameter of the elongated tubular body 18. A ring or stop 22 is positioned to extend radially outwardly at the junction of the shoulder 20 and the tubular body 18. An opening 24 (FIG. 6) extends through the length of the base dilator 12. The opening is sized to permit the dilator 10, and particularly, the base dilator 12, to be positioned over a guide wire (not shown) which is disposed into a desired tissue target, such as, but not by way of limitation, a hollow organ. The guide wire permits the base dilator 12, which is the smallest diameter in the series of telescoping tubes contained in the stoma dilator 10, to be positioned over the wire and through the tissue opening and into the target tissue, for example, a patient's stomach. The base dilator 12 has a length 26 (FIG. 7) which is desirably longer than the other tubes comprising the stoma dilator 10, to permit this initial introduction into the stomach.

Figure 5:
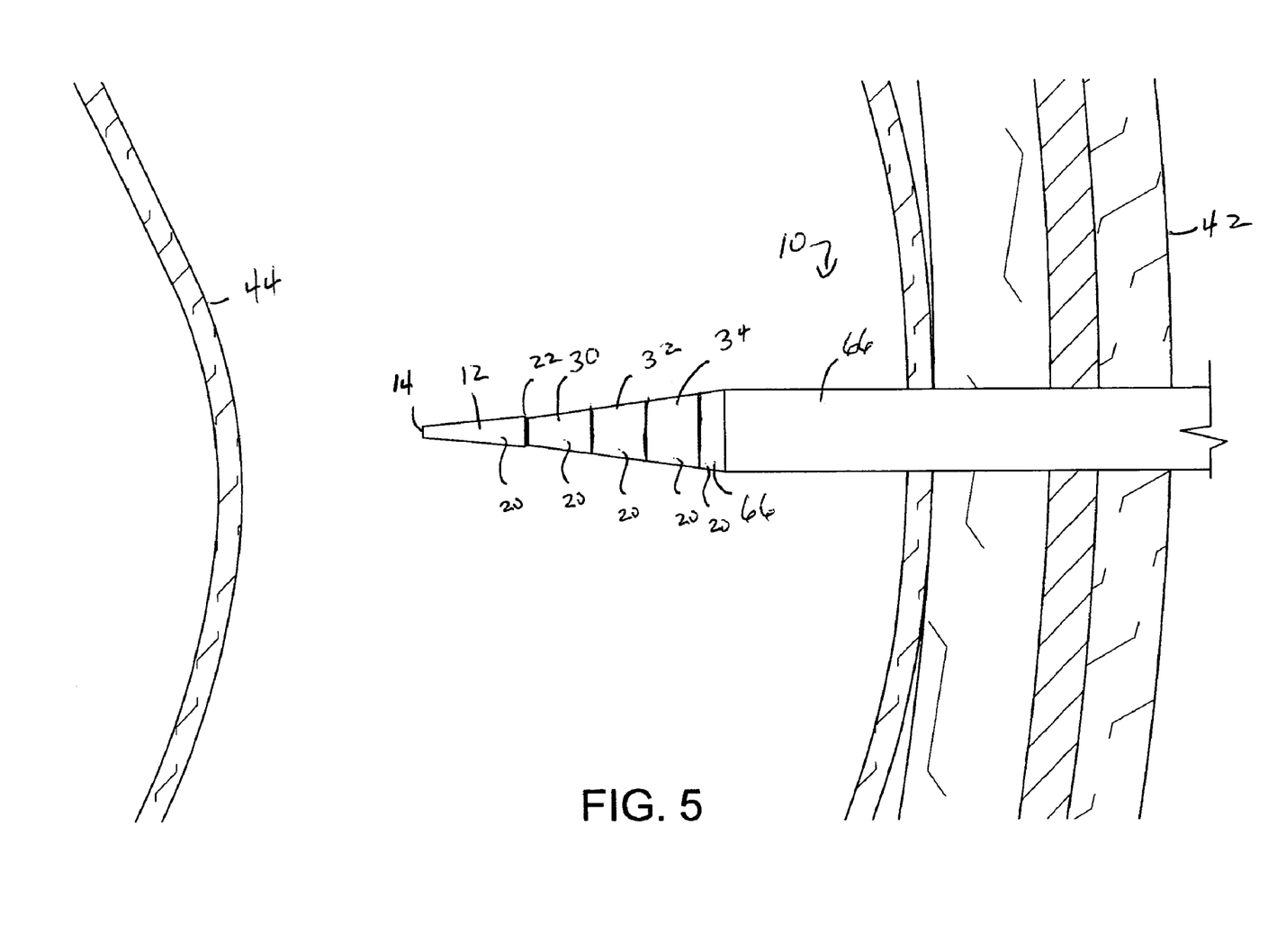
FIG. 5 is a side elevational view of the distal ends and stops provided on each dilator which cooperate to provide a taper of all of the dilators of the stoma dilator.
Figure 6:
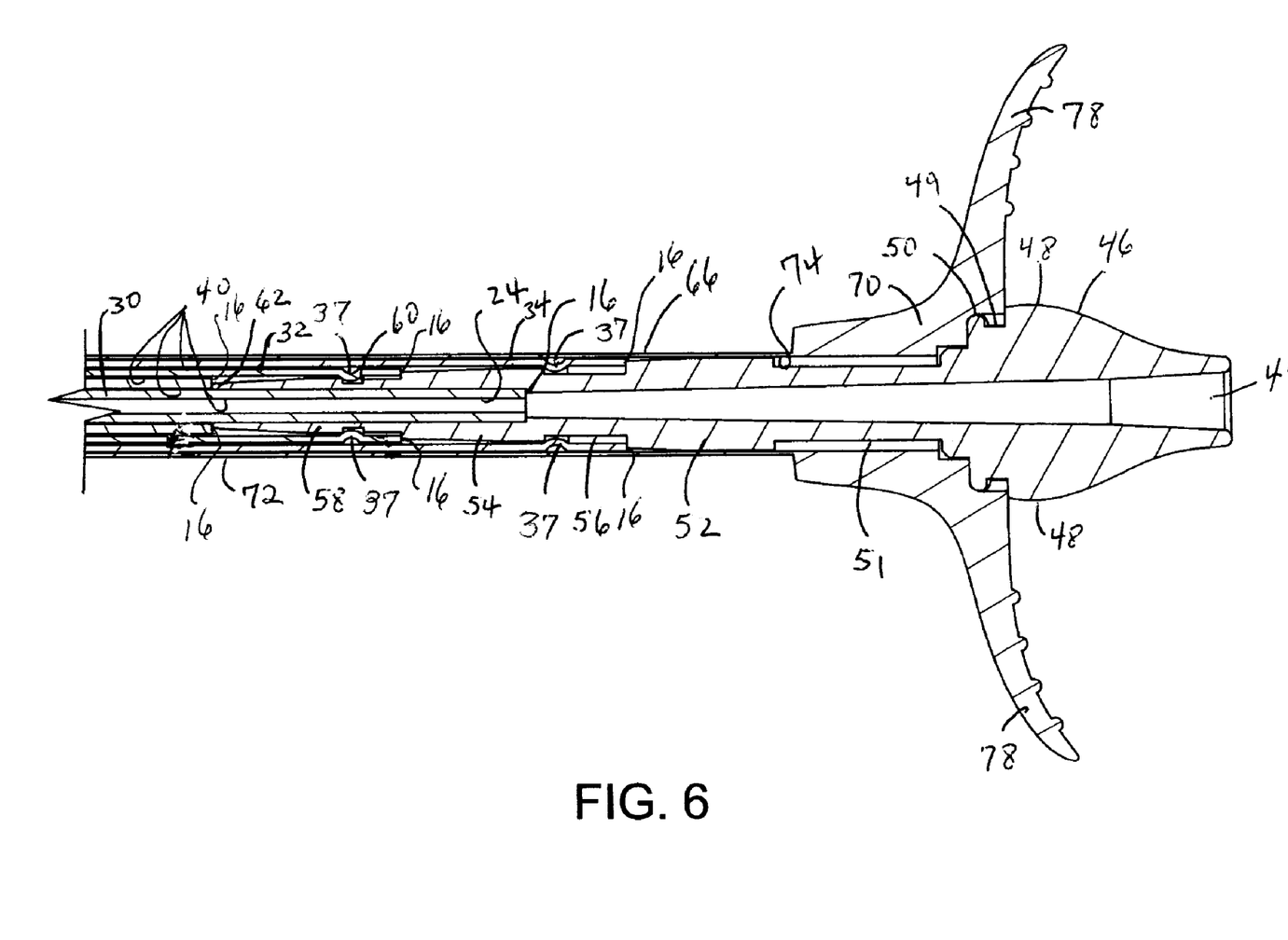
FIG. 6 is a partial sectional view of FIG. 1, showing the dilator positioner.
Figures 9, 10:
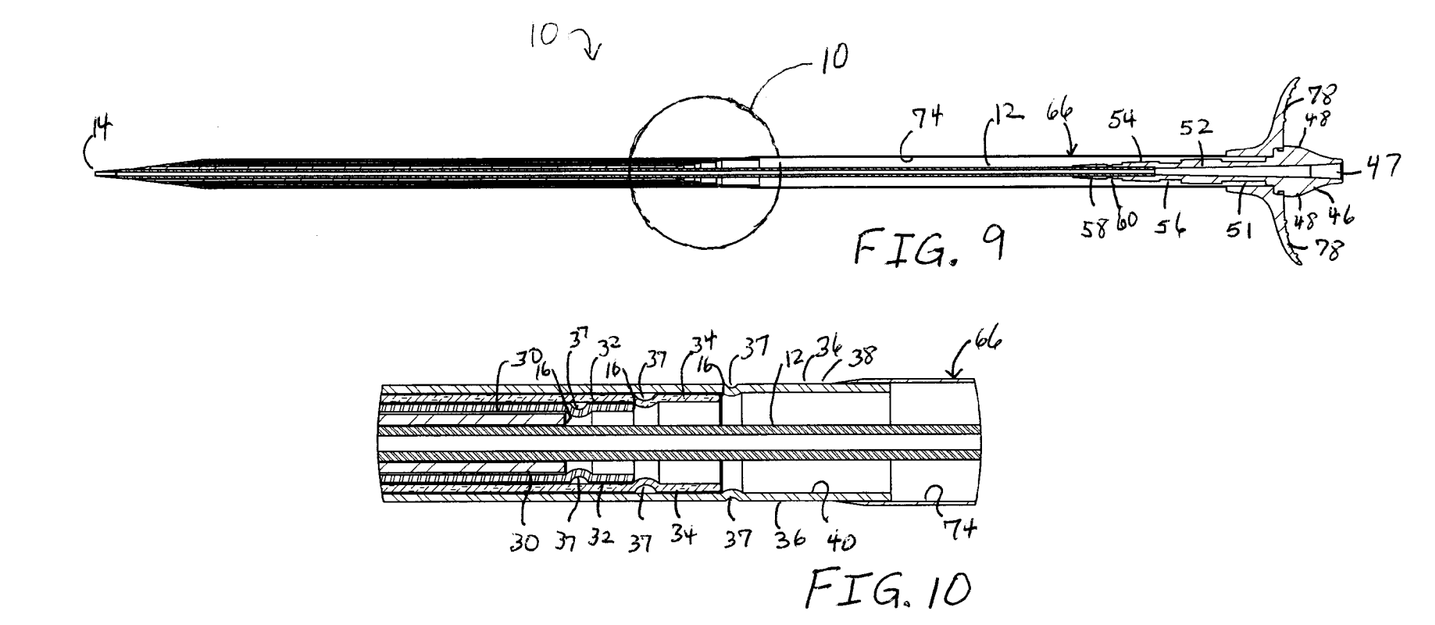
FIG. 9 is a sectional view similar to FIG. 7, but showing a stoma dilator having a base dilator and a second, third, fourth and fifth dilators, the dilators deployed toward the distal end of the first or base dilator, thereby forming a continuous taper and illustrating the deployment desired to form a tissue opening or stoma.
FIG. 10 is a partial sectional view of FIG. 9, taken along line 10.

As illustrated in FIGS. 1-3 and 5, the stoma dilator desirably, but not by way of limitation, includes four additional dilators, namely, a second dilator 30, a third dilator 32, and a fourth dilator 34. A fifth dilator 36 is illustrated only in FIGS. 9 and 10. These dilators are coaxially stacked on the base dilator 12, so that each may be telescopically moved into position in a tissue dilating procedure. All dilators 12, 30, 32, 34 and 36 used in the stoma dilator 10 are positioned in a longitudinal coaxial alignment. Each of the dilators 30, 32, 34 and 36, respectively, include, similar to the base or first dilator 12, a first end 14, a proximal end or tail end 16, and an elongated tubular body 18. Each of the second, third, fourth and fifth dilators 30, 32, 34 and 36, respectively, also include a tapered shoulder 20, and the third, fourth, and fifth dilators 32, 34, and 36 include an internal ring or stop 37 positioned near a proximal end or tail end 14 thereof (FIGS. 6, 9 and 10). An opening 24 extends through each second, third, fourth and fifth dilators 30, 32, 34 and 36.

Each of the first, second, third, fourth and fifth dilators 12, 30, 32, 34 and 36 having an outer surface 38 which defines an outer diameter, as shown in FIGS. 1-3, 5 and 6. Each outer surface 38 of the dilators 12, 30, 32, 34 and 36 have a an outer diameter which is slightly larger than a diameter of an inner surface 40 of a dilator which is disposed at least partially over it. For example, the inner surface 40 of the base or first dilator 12 has a in inner surface 40 which has a diameter large enough to moveably and slideably accept a guide wire therethrough (not shown). Accordingly, the second dilator 30 has an inner surface 40 which has a diameter large enough to permit the base or first dilator 12 to slidingly move therethrough. Accordingly, the same is true for the relationship between the second and third 30 and 32 dilators, the third and fourth dilators 32 and 34, and the fourth and fifth dilators 34 and 36.

Figure 7:
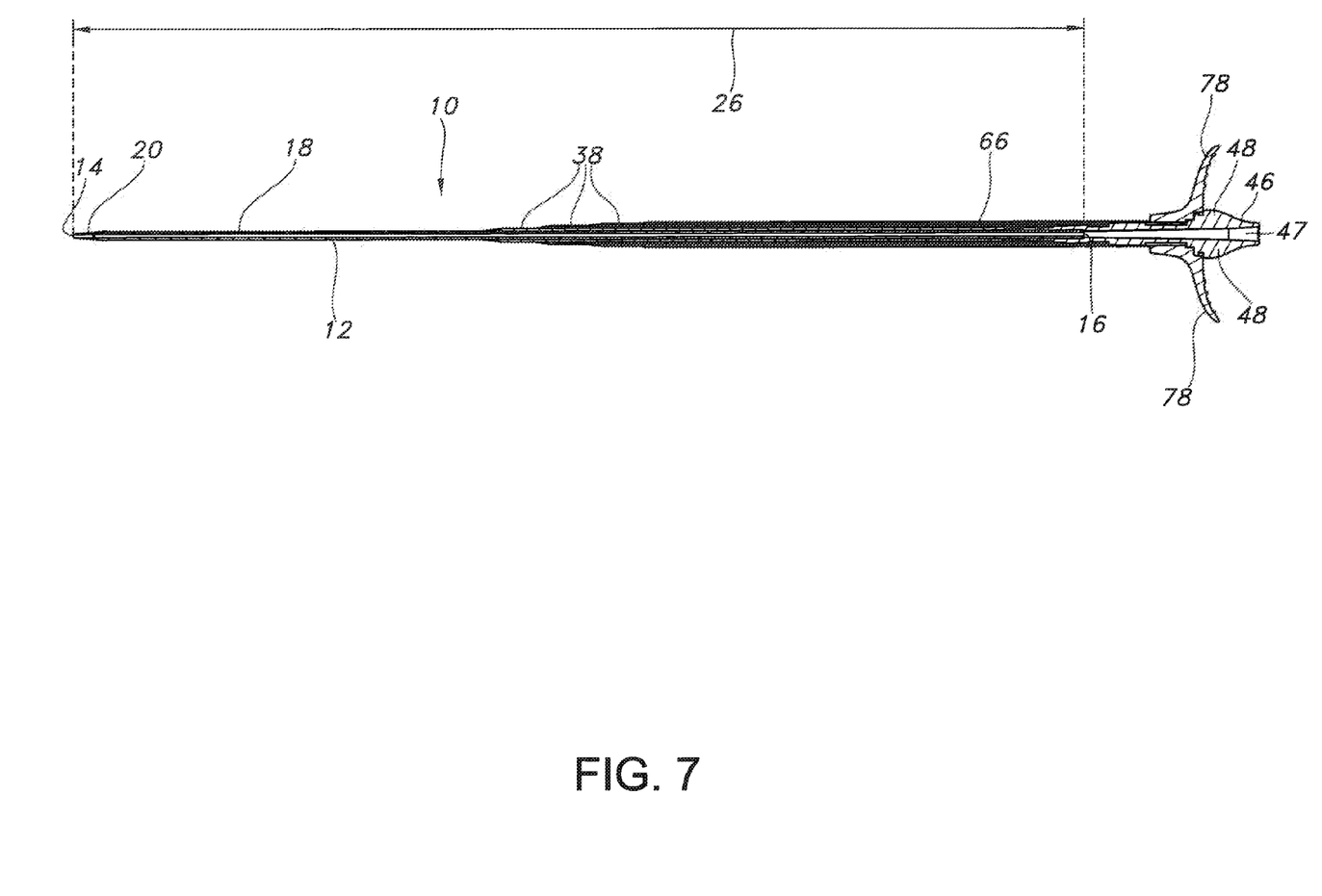
FIG. 7 is a sectional view of FIG. 1, taken along lines 7-7.

It will be understood that the inner diameter of the dilators, for example, the third 32 dilator, is desirably large enough to slide over the dilator positioned next to its inner surface 40, that is, the second dilator 30. There is desirably little space between the inner surface 40 of one dilator, such as the third dilator 32, and an underlying outer surface 38 of the adjacent dilator, such as the second dilator 30, as illustrated in FIGS. 6 and 7. Desirably, there is only sufficient space to permit the sliding movement, or telescoping, of the respective dilators 12, 30, 32, 34 and 36. The distal end 14 of each dilator 12, 30, 32, 34, 36 is formed to flush its underlying dilator because it is undesirable to have enough space that blood, or other bodily fluids enter this space.

Figure 1:
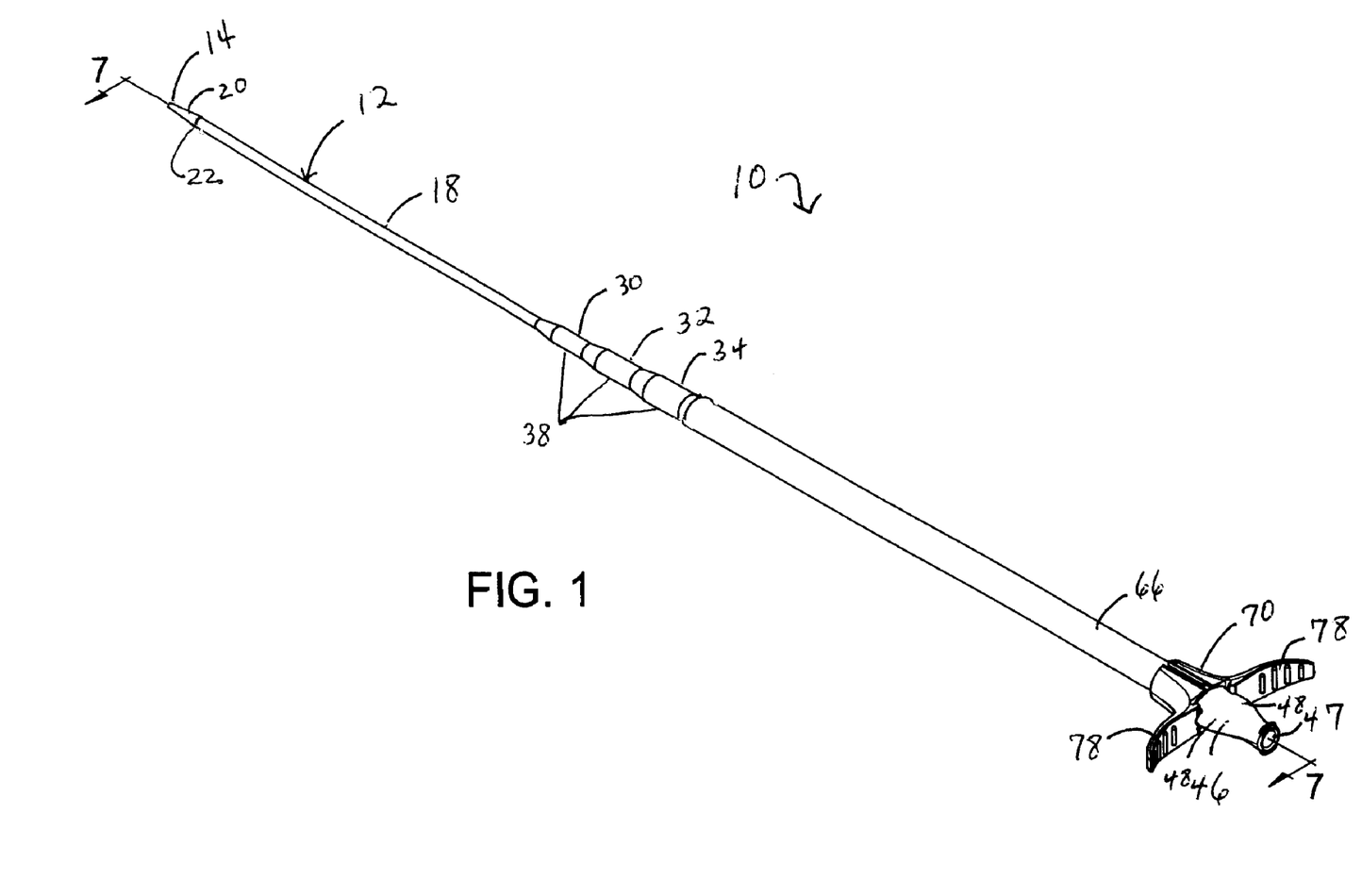
FIG. 1 is a perspective view of a top of a stoma dilator of the present invention, which includes a base dilator, a second, third and fourth dilator, and a sheath.
Figure 2:
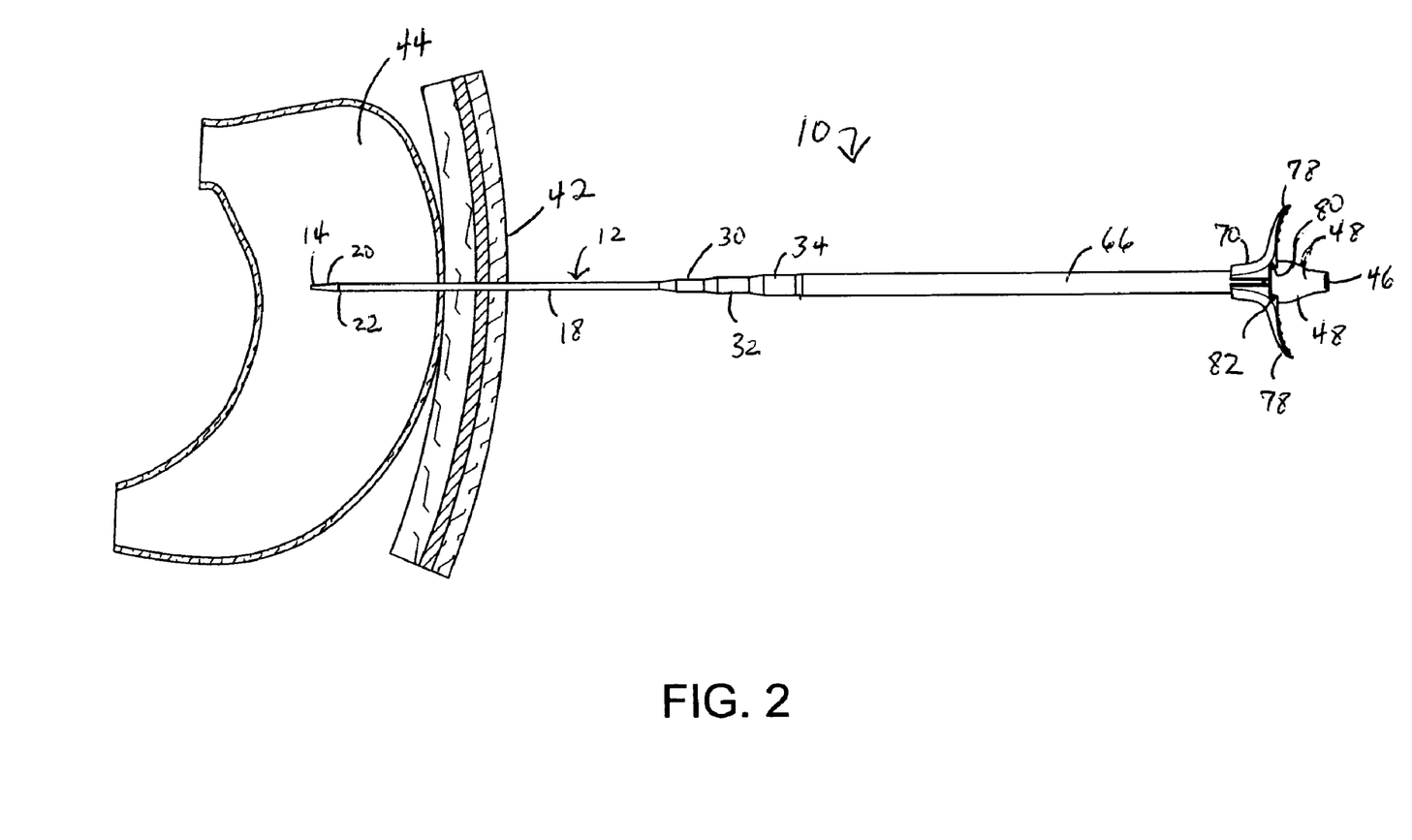
FIG. 2 is a side elevational view of the stoma dilator of FIG. 1, showing a base dilator positioned through a patient's skin and abdominal wall and into a patient's stomach.
Figure 3:
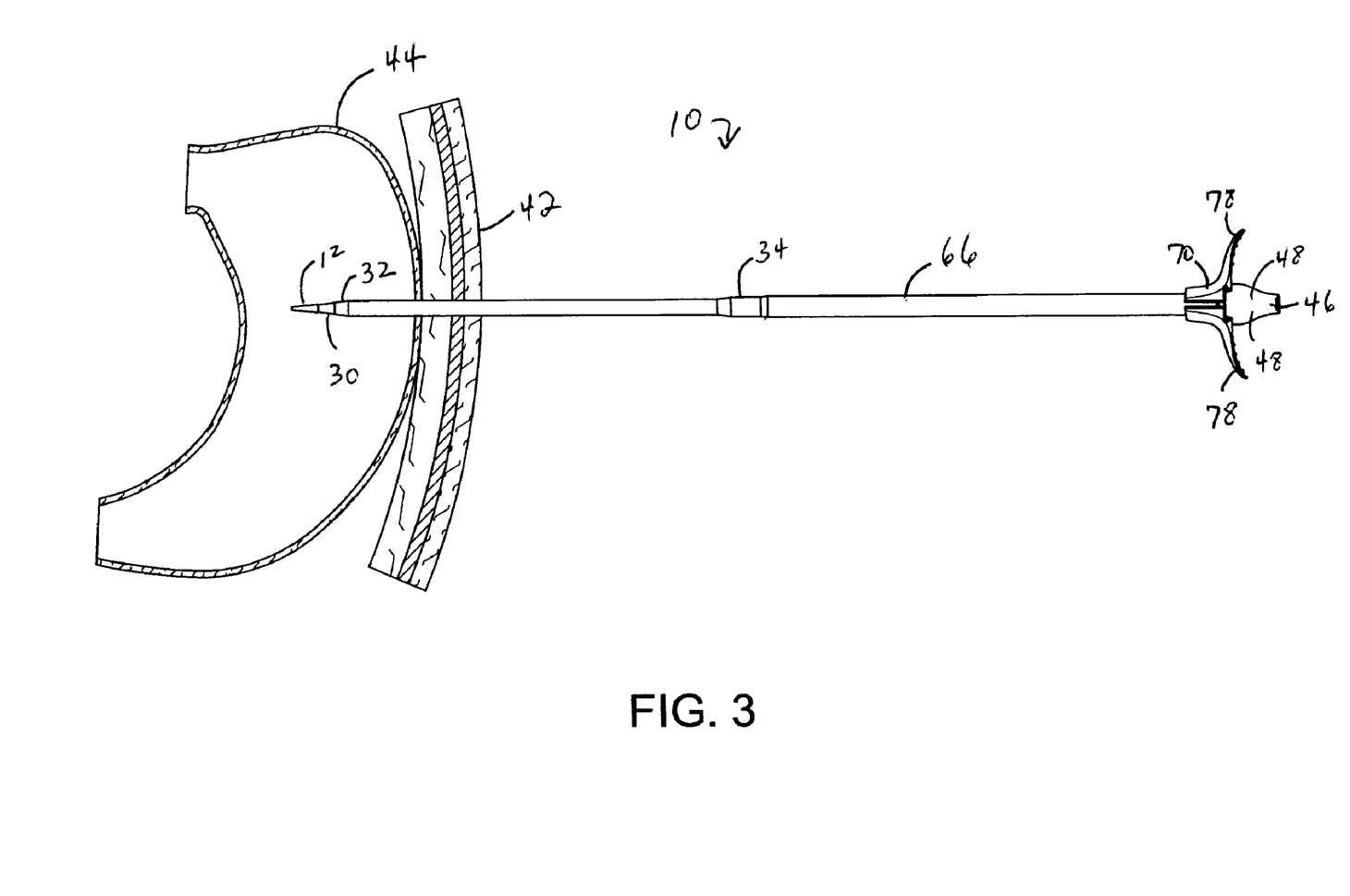
FIG. 3 is a side elevational view similar to FIG. 2, but showing two additional dilators positioned over the base dilator.

The base or first dilator 12 provides a primary support and operates as a mounting base for each additional elongated, tubular dilators 30, 32, 34 and 36 which are telescopically positioned around the base or first dilator. For example, the base or first dilator 12 is shown in FIG. 1 positioned through a patient's skin 42 and into a patient's stomach 44. The tubular body 18 is structured to have a uniform diameter and outer surface 38. The taper between the first end 14 and the tubular body 18 enables gradual a dilation of tissue. Accordingly, each successive dilator 30, 32, 34, 36 has a cooperating taper which provides a continuous taper (FIG. 5) of the stoma dilator 10, as illustrated in FIG. 2, which permits a gradual dilation and causes less trauma to a patient's tissue. The stop 22 on dilator 12 and the stop on each dilator 30, 32, 34 and 36, as shown in FIGS. 6, 9 and 10, prevents one of the dilators to advance over the other when positioned inside of a patient's body. Therefore, health care provider's are more easily aware of the position of each dilator 12, 30, 32, 24, 36 with respect to the tissue target of the dilator 10.

The tail end 16 of the base or first dilator 12 differs from the tail end 16 of the other dilators 30, 32, 34 and 36, as shown in FIGS. 1, 6 and 7. A hub assembly is disposed thereon, and it includes a hub 46 having an opening 47 therethrough in communication with the opening 24 formed in the base or first dilator 12. The hub 46 desirably has an ISO female luer lock positioned on the tail end 16 of the base or first dilator 12. The hub 46 has a pair of opposing wings 48 positioned opposite each other on the hub 46, which aid in grasping the hub 46. Each wing 48 has a groove 49 therein. A base 50 of the hub 46 is positioned therebelow.

The hub assembly also includes a dilator positioner. A portion of the dilator positioner includes a plurality of radially-disposed bars which are positioned in separate groups on the base or first dilator 12 below the hub 46, as illustrated in FIGS. 6, 7, 9 and 10. The separate groups of bars are desirably spaced-apart from the wings 48 of the hub 46 via a groove 51 which is adjacent to the base 50. The groups of radially-disposed bars are axially aligned on a portion of the outer surface 38 of the base or first dilator 12, and are separated into separate groups, each group having a different diameter. The first group of bars or first bars 52 comprises, for example, but not by way of limitation, four bars, which have a relatively largest outer diameter of the group. The second group of bars or second bars 54, are spaced-apart from the first bars via a groove 56. The second bars 54 have a relatively intermediate diameter, relative to a third group of bars or third bars 58. The third bars 58 have a smallest diameter, relative to the second bars 54 and the first bars 52. The third bars 58 are spaced-apart from the second bars 54 via a groove 60. An end 62 of the dilator positioner is also desirably utilized; the end 62 is positioned next to the third bars 58. Each set of grooves 51, 56, and 60 may include bars or other protuberances, but will be smaller in outer diameter than the bars 52, 54 or 58 which are next to it.

The proximal ends or tail ends 16 of the third, fourth and fifth dilators 32, 34, 36, as noted previously, each desirably have an inner radial ring or stop 37 formed near the tail end 16 on an inner surface 40 thereof. These stops 37 cooperate with the end 62 and the first, second and third bars 52, 54, 58 to retain the second, third, fourth and fifth dilators 30, 32, 34, 36 on the hub or base dilator 12 in an undeployed position and to prevent them from being deployed prematurely, and are a part of the dilator positioner. The undeployed position of the second, third, fourth and fifth dilators 30, 32, 34, 36 is illustrated in FIGS. 1, 2, 6 and 7; the deployed position of the second, third, fourth and fifth dilators 30, 32, 34, 36 is illustrated in FIGS. 5, 9 and 10. In the absence of the components of the dilator positioner, dilators on a hub can be deployed prematurely, when an underlying dilator is deployed, and the friction between dilators can cause one or more of the overlying dilators to also be deployed. The components of the dilator positioner prevents this occurrence.

As illustrated in FIGS. 6 and 7, in the undeployed position, a portion of the dilator positioner assist in holding the dilators in a staggered coaxial alignment. The end 62 contacts the proximal or tail end 16 of the second dilator 30 into a telescoping position over the first or base dilator 12, and prevents positioning of the second dilator 30 closer to the hub 46. The third bars 58 position the stop 37 on the third dilator 32 so that it contacts the groove 60 and the proximal or tail end 16 of the third dilator 32 contacts the second bars 54 to position the third dilator 32 in a telescoping position over the second dilator 30 and to prevent movement of the third dilator 32 toward the hub 46. The stop 37 on the fourth dilator 34 is positioned in the groove 56 between the second bars 54 and the first bars 52. The proximal or tail end 16 of the fourth dilator 34 is positioned against the first bars 52 to position the fourth dilator 34 in a telescoping position over the third dilator 32 and to prevent movement of the fourth dilator 34 toward the hub 46.

The dilator positioner prevents one or more of the smaller dilators from getting frictionally retained within one of the larger dilators, so that all dilators are readily and sequentially positioned and that at least a portion of the distal or first end 14 of each dilator 12, 30, 32, 34, 36 (FIGS. 9 and 10) is accessible. The dilator positioner also holds the dilators 30, 32, 34, 36 in place, so that one or more of the dilators cannot be removed or fall off of a proximal end of the stoma dilator 10. The dilator positioner, via the bars 52, 54, 58 and grooves 51, 56, 60, as well as the radially positioned stops 37 near the proximal ends 16 of the dilators 30, 32, 34 and 36 permits proper deployment of the dilators, as illustrated in FIGS. 6, 9 and 10. The components of the dilator position act to present the dilators in a staggered coaxial alignment, so that the distal end of each dilator presents at least portion that may be grasped by a health care practitioner and moved for tissue dilation.

Figure 4:
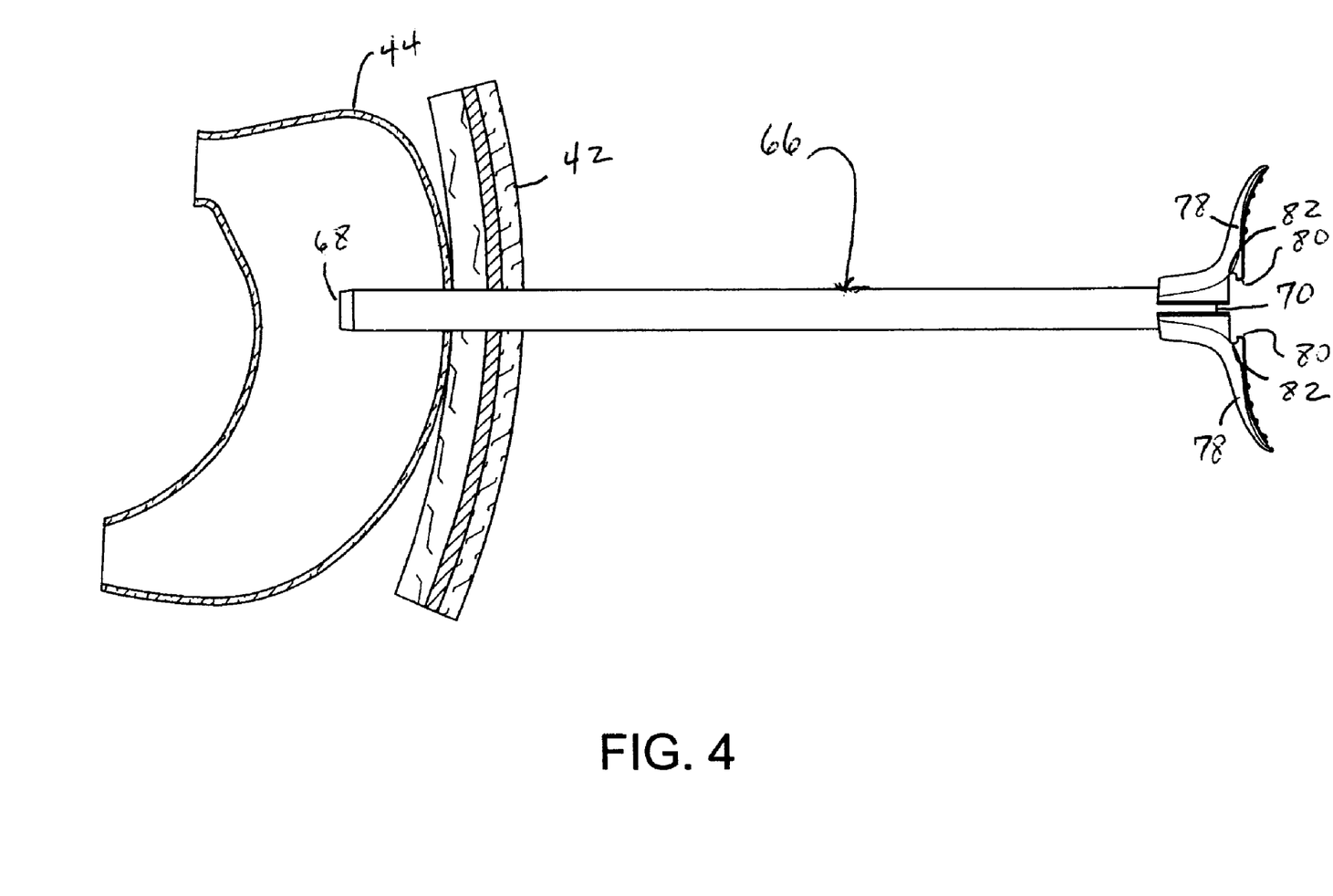
FIG. 4 is a side elevational view of the sheath of the stoma dilator positioned through the stoma, the base dilator and plurality of dilators removed from within the sheath.
Figure 8:
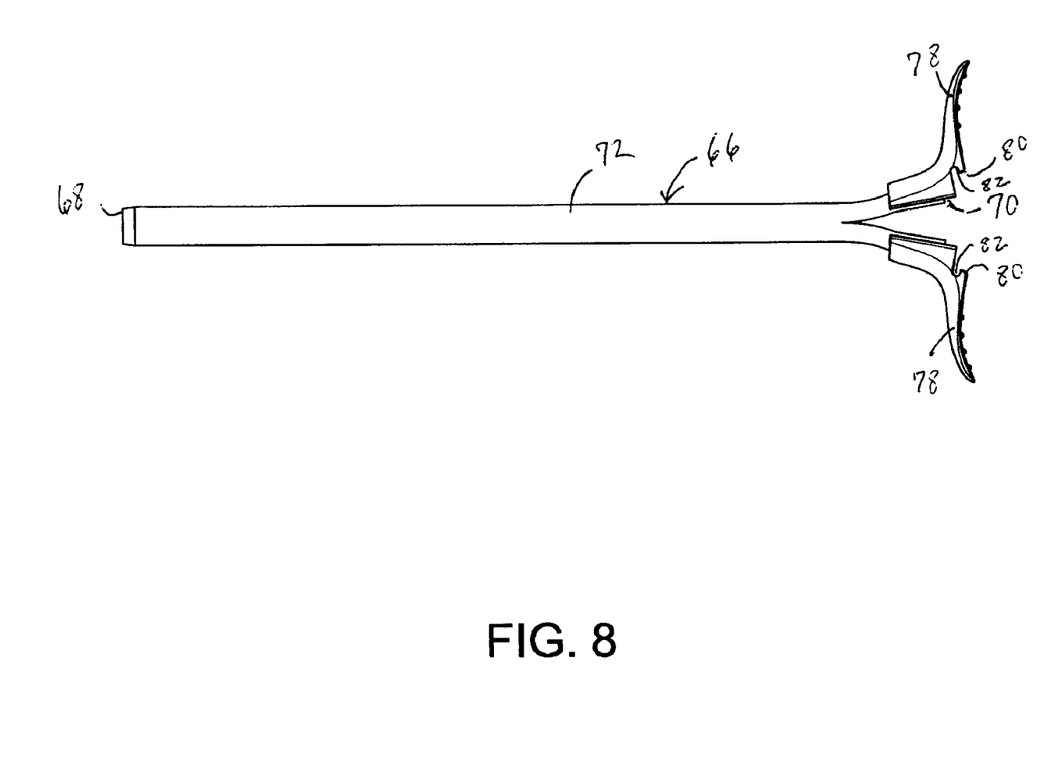
FIG. 8 is a side elevational view of the sheath, showing the handles splitting the sheath into two parts to permit the sheath to be peeled away from a device inserted therein.

As also illustrated in FIGS. 1, 4 and 8, the stoma dilator 10 desirably includes a sheath 66 which is positioned in coaxial alignment over the fourth dilator 34 (FIGS. 1-8) or the fifth dilator 36 (FIGS. 9 and 10). It will be understood that the sheath 66 is desirably positioned over the outer-most dilator of the plurality of dilators.

The sheath 66 includes a distal end 68 and an opposing proximal end 70. A longitudinal cylindrical tube or sheath body 72 is positioned therebetween. The sheath body 72 has an opening therethrough and an inner diameter defined by an inner surface 74 that is only slightly larger than an outer diameter of the outer surface 38 of the outer most dilator. The diameter size of the sheath 66 facilitates movement of the sheath over the outer surface 38 of the outermost dilator, but does not facilitate movement of bodily fluids through the space between the sheath 66 and the outermost dilator.

The proximal end 70 of the sheath 66 includes a pair of handles 78 which are positioned in a spaced-apart and opposing relationship on the sheath 66. Each handle 78 includes a flange 80 positioned adjacent the hub 46 and a recess 82 positioned thereunder. A portion of each flange 78 extends into the groove 49 next to the base 50 of the hub 46, while a portion of the base 50 extends into the recess 82 positioned below each flange 80 of each handle 78. These components cooperate to hold the sheath 66 in an engaged, fixed, non-deployed position against the hub 66 relative to the dilators 12, 30, 32, 34 (FIGS. 1-8) and 36 (FIGS. 9 and 10). However, by turning the hub 46 ninety (90) degrees, the above-referenced components are rotated out of an engaged alignment, permitting movement of the sheath 66 over the outer surface 38 of the outermost dilator. In addition, the sheath 66 may be coupled to a portion of the stoma dilator 10 via a releasable adhesive (such as a pressure sensitive adhesive) and so forth (not shown). If coupled via any adhesive, rotation of the sheath 66 desirably will release the release the adhesive, permitting the sheath 66 to be moved. The sheath 66 may be placed through the stoma or tissue opening, and the stoma dilator 10 may be removed. The sheath 66 may permit a device to be positioned therethrough via its opening. The sheath may be peeled away from such a device placed therethrough, to permit at least a portion of such a device to be retained in the tissue opening or stoma. The sheath 66 may be removed by pushing the handles 78 toward the distal end 68 of the sheath 66, which causes the sheath 66 to begin to separate at the proximal end 70, and down the sheath body 72 between the handles 78. This separation extends down the body 72 to the distal end 68, to permit the sheath 66 to be withdrawn from around such a device.

In a method of use, for example, in providing an opening in a patient's tissue, such as forming a stoma into a target organ or blood vessel, a stoma dilator 10 is desirably provided, as shown in FIG. 1. A wire may desirably be disposed via a lumen of an introducer needle (not shown) through a patient's skin 42 and into a target organ, such as a patient's stomach 44. The needle is withdrawn and the wire is desirably retained in place (not shown). The base or first dilator 12 is desirably positioned over the wire (not shown), and it is moved by manual manipulation of a health care practitioner to follow the wire through the patient's skin 42 and into the stomach 44 to begin the creation of the tissue opening or stoma (FIG. 2). The next-sized dilator, i.e., the second dilator 30, is then manually moved over the base or first dilator 12, until the distal end or first end 14 contacts the stop 22 on the first end 14 of the first or base dilator 12. The third dilator 32 is manually moved over the second dilator 30, until the stop 37 near the proximal end or tail end 16 of the third dilator 32 contacts the proximal end or tail end 16 of the second dilator 30, as shown in FIGS. 9 and 10. The fourth dilator 34 is then, in sequence, manually disposed over the third dilator 32, until the stop 37 near the proximal or tail end 16 of the fourth dilator 34 contacts the proximal end or tail end 16 of the third dilator 34. Finally, if a fifth dilator 36 is present, as illustrated in FIGS. 9 and 10, it is positioned over the fourth dilator 34, until the stop 37 near the proximal end or tail end 16 the fifth dilator 36 contacts the proximal end or tail end 16 of the fourth dilator 34. At this point, the tissue opening or stoma is sufficiently dilated to move the sheath 66 in place.

Another portion of the dilator positioner, namely, the stop 22 on the base dilator 12 and the stops 37 on at least some of the plurality of dilators, in this instance, the third, fourth and fifth dilators 32, 34 and 36, cooperate as the other portion of the dilator positioner to permit proper deployment of the dilators toward and adjacent the distal or first end 14 of the base dilator 12, so that each dilator has a distal end 14 which is graspable by a health care practitioner to move into a cooperative deployment, as illustrated in FIGS. 9 and 10, and which provides a continuous taper of the distal end of the stoma dilator 10, as shown in FIG. 5. It will be appreciated that the stops 22 and 37 operate such that one dilator of the plurality of dilators, in this instance, the second dilator 30, does not have and does not need a stop to be held in proper alignment in a deployed position.

To position the sheath 66, the sheath 66 is rotated ninety (90) degrees with respect to the hub 46 to release the sheath 66 from it's releasable connection with the hub 46. That is, the portion of the base 50 of the hub 46 is moved out of the recess 82 below the flange 80, and the portion of the flange 80 of the handle 78 is moved out of the groove 49 next to the base 50. This action moves the referenced components in into a non-engaged position, thereby permitting movement of the sheath 66 over the outer surface 38 of the outermost dilator.

The distal end 68 of the sheath is blunted and not tapered, so that it may extend past one or more of the first ends 14 of the first, second, third, fourth or fifth dilators 12, 30, 34, 36. Once the sheath 66 is in position through the tissue opening, the stoma dilator 10, that is, the base dilator 12 and the plurality of dilators 30, 32, 34 (FIGS. 1-8) and 36 (FIGS. 9 and 10), is removed by moving it out of the tissue opening. The wire is desirably removed at least with the stoma dilator 10 (not shown). The sheath 66 is desirably left in position in the stoma (FIG. 4). A device, such as, but not by way of limitation, an enteral feeding tube, may be positioned through the sheath 66 and at least a portion of the device may be positioned in the stomach and secured through normal means, such as inflation of a bolster at the distal end thereof (not shown). Once such a device is in place, the handles 78 of the sheath 66 or pushed toward the distal end 68 of the sheath 66, so that the proximal end 70 of the sheath 66 will start splitting apart between the handles 78 (FIG. 8. Desirably, the sheath 66 will split apart from the proximal end 70 to the distal end 68, providing two separate portions, each retaining a handle (not shown). The sheath 66 is desirable withdrawn from the tissue opening or stoma and discarded.

The opening 47 through the hub and through the base or first dilator 12 permits removal of the wire (not shown) at any time during the procedure, as well as luminal access to the stomach, for purposes of injecting fluids or contrast media, or withdrawing fluid from the stomach 44. The hub 46 may also include a Tuohy-Borst connector (not shown). The Tuohy-Borst connector may be tightened to lock the dilator onto the guide wire and prevent fluids from escaping through the opening 47 in the hub 46 and the opening 24 in the base or first dilator 12.

The stoma dilator 10 is desirably constructed from a medical grade plastic. More desirably, the stoma dilator 10 may be constructed from high density polyethylene. It will be understood that the stoma dilator 10 may be constructed in different sizes, to a to accommodate tissue openings into different organs or blood vessels in a human body. For use in a gastrostomy, however, desirably the base or first dilator 12 is an 8 French size. For this use, the second dilator 30 is desirably a 12 French size, the third dilator 32 is desirably a 16 French size, the fourth dilator 34 is desirably a 20 French size, and, if present, the fifth dilator 36 is desirably a 24 French size. The sheath is desirably a 26 French size when a fifth dilator is used; it will be appreciated that a smaller size sheath will be used over the fourth dilator if only four dilators are present. The peel-away sheath and hub assembly are desirably constructed from a medical grade high density polyethylene.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. A stoma dilator comprising:
a base dilator having a distal end, a proximal end, and a tubular body positioned therebetween, a hub positioned on the proximal end of the base dilator, at least a portion of a dilator positioner is provided therewith, the distal end includes a stop thereon, and the base dilator is formed to include an opening therethrough, wherein the base dilator is configured to be positioned over a wire into a patient's tissue; and
a plurality of dilators disposed in an initial, un-deployed configuration coaxially stacked on the base dilator, each of the plurality of dilators including a tapered distal end, a proximal end, and a tubular body positioned therebetween, another portion of the dilator positioner comprising a stop positioned proximally on each of at least two or more of the plurality of dilators, wherein the portions of the dilator positioner cooperate to position the plurality of dilators such that a portion of each distal end of each dilator is graspable by a health care practitioner for movement from its initial, un-deployed configuration coaxially stacked on the base dilator to a deployed position, wherein the stop on the base dilator and the more than one stop on the plurality of dilators cooperate to form a continuous taper of a distal end of the stoma dilator when the plurality of dilators are positioned in a deployed position.

2. The stoma dilator of claim 1, wherein a portion of the dilator positioner is positioned adjacent the hub, and wherein at least another portion of the dilator positioner is positioned about at least a portion of an outer surface of the base dilator.

3. The stoma dilator of claim 1, wherein at least a portion of the dilator positioner comprises at least two groups of a plurality of bars, wherein each group of bars is spaced-apart axially about the base dilator and a groove separates each group of bars axially on the base dilator, and wherein each group of bars comprises a different outer diameter in its position about the base dilator.

4. The stoma dilator of claim 1, wherein more than one of the plurality of dilators includes a radially positioned ring on an inner surface of the dilator, and wherein the ring comprises a stop which cooperates with the dilator positioner to move at least one dilator into a position to dilate a patient's tissue.

5. A stoma dilator comprising:
a base dilator having a distal end, a proximal end, and a tubular body positioned therebetween, a hub positioned on the proximal end and at least a portion of a dilator positioner provided therewith, the base dilator formed to include an opening therethrough, the base dilator configured to be positioned over a wire into a patient's tissue;
a first portion of the dilator positioner comprising at least two groups of a plurality of bars, wherein each group of bars is spaced-apart axially about the base dilator and a groove separates each group of bars axially on the base dilator, and wherein each group of bars comprises a different outer diameter in its position about the base dilator; and
a plurality of dilators disposed in an initial, un-deployed configuration coaxially stacked on the base dilator, each of the plurality of dilators having a tapered distal end, a proximal end, and a tubular body positioned therebetween, more than one of the plurality of dilators positioned by at least another portion of the dilator positioner comprising a stop positioned proximally on each of at least two or more of the plurality of dilators such that a portion of each distal end is exposed from beneath another dilator and is graspable by a health care practitioner for movement from its initial, un-deployed configuration coaxially stacked on the base dilator to a deployed position such that a smaller diameter dilator does not become inaccessible inside of a larger diameter dilator.

6. The stoma dilator of claim 5, wherein at least another portion of the dilator positioner is positioned on more than one of the plurality of dilators.

7. The stoma dilator of claim 6, wherein the more than one of the plurality of dilators includes a radially positioned ring comprising a stop on an inner surface of the dilator, and wherein the stop cooperates with at least one other dilator to telescopically position at least one dilator into a position to dilate a patient's tissue.

8. The stoma dilator of claim 5, wherein the distal end of the base dilator has a stop thereon, and wherein more than one of the plurality of dilators includes a stop positioned near a proximal end thereof.

9. The stoma dilator of claim 8, wherein the stop on the more than one of the plurality of dilators cooperate, when the distal end and proximal end of each of the plurality of dilators which have a stop are positioned against a stop, to form a continuous taper of the distal end of the stoma dilator.

* * * * *